US006492099B1

United States Patent
Boldea et al.

(10) Patent No.: US 6,492,099 B1
(45) Date of Patent: Dec. 10, 2002

(54) METHOD FOR PURIFYING FREE-BASE P-PHENYLENEDIAMINE-TYPE PHOTOGRAPHIC COLOR DEVELOPERS

(75) Inventors: Lucian Boldea, Jonesborough, TN (US); Phillip Montgomery Hudnall, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/893,801

(22) Filed: Jun. 28, 2001

(51) Int. Cl.$^7$ ............................................... G03C 7/413
(52) U.S. Cl. .......................................... 430/467; 203/2
(58) Field of Search ................................ 430/467; 203/2

(56) References Cited

U.S. PATENT DOCUMENTS

| | | |
|---|---|---|
| 4,876,174 A | 10/1989 | Ishikawa et al. |
| 4,892,804 A | 1/1990 | Vincent et al. |
| 5,273,865 A | 12/1993 | Loiacono et al. |
| 5,354,646 A | 10/1994 | Kobayashi et al. |
| 5,558,893 A * | 9/1996 | Muraldihara ................. 426/286 |
| 5,646,327 A | 7/1997 | Burns et al. |
| 5,660,974 A | 8/1997 | Marrese et al. |
| 5,702,873 A | 12/1997 | Twist |
| 5,709,982 A | 1/1998 | Marrese et al. |
| 5,723,268 A | 3/1998 | Fyson |
| 6,017,687 A | 1/2000 | Darmon et al. |
| 6,020,113 A | 2/2000 | Abe |
| 6,077,651 A | 6/2000 | Darmon et al. |
| 6,228,567 B1 | 5/2001 | Darmon et al. |

FOREIGN PATENT DOCUMENTS

| | | |
|---|---|---|
| EP | 0 204 372 A1 | 12/1986 |
| EP | 0 434 097 A1 | 6/1991 |
| EP | 0 530 921 A1 | 3/1993 |
| EP | 0 793 141 A2 | 9/1997 |
| EP | 0 800 111 A1 | 10/1997 |

OTHER PUBLICATIONS

R. L. Bent et al., "Chemical Constitution, Electrochemical, Photographic and Allergenic Properties of p–Amino–N–dialkylanilines," Journal of the American Chemical Society, 1951, pp. 3100–3125, vol. 73, United States.
Klaus J. Erdweg, "Molecular and Short–Path Distillation," Chemistry and Industry, May 2, 1983, pp. 342–345, United States.

* cited by examiner

Primary Examiner—Hoa Van Le
(74) Attorney, Agent, or Firm—Michael Blake; Bernard J. Graves, Jr.

(57) ABSTRACT

A process for purifying p-phenylenediamine color developers in their free-base form. The process includes subjecting a solution containing p-phenylenediamine-type free base color developer to short path distillation which includes at least one of falling film evaporator, thin film evaporator, wiped film evaporator, or short-path evaporator.

Another aspect is a method for preparing an acid salt from a p-phenylenediamine free base color developer. The method includes the steps of: a) dissolving a purified p-phenylenediamine free base derived from the short path distillation process in an organic solvent; b) contacting the dissolved free base distillate with an appropriate mineral acid; and c) crystallizing the color developer in the acid salt form.

13 Claims, 1 Drawing Sheet

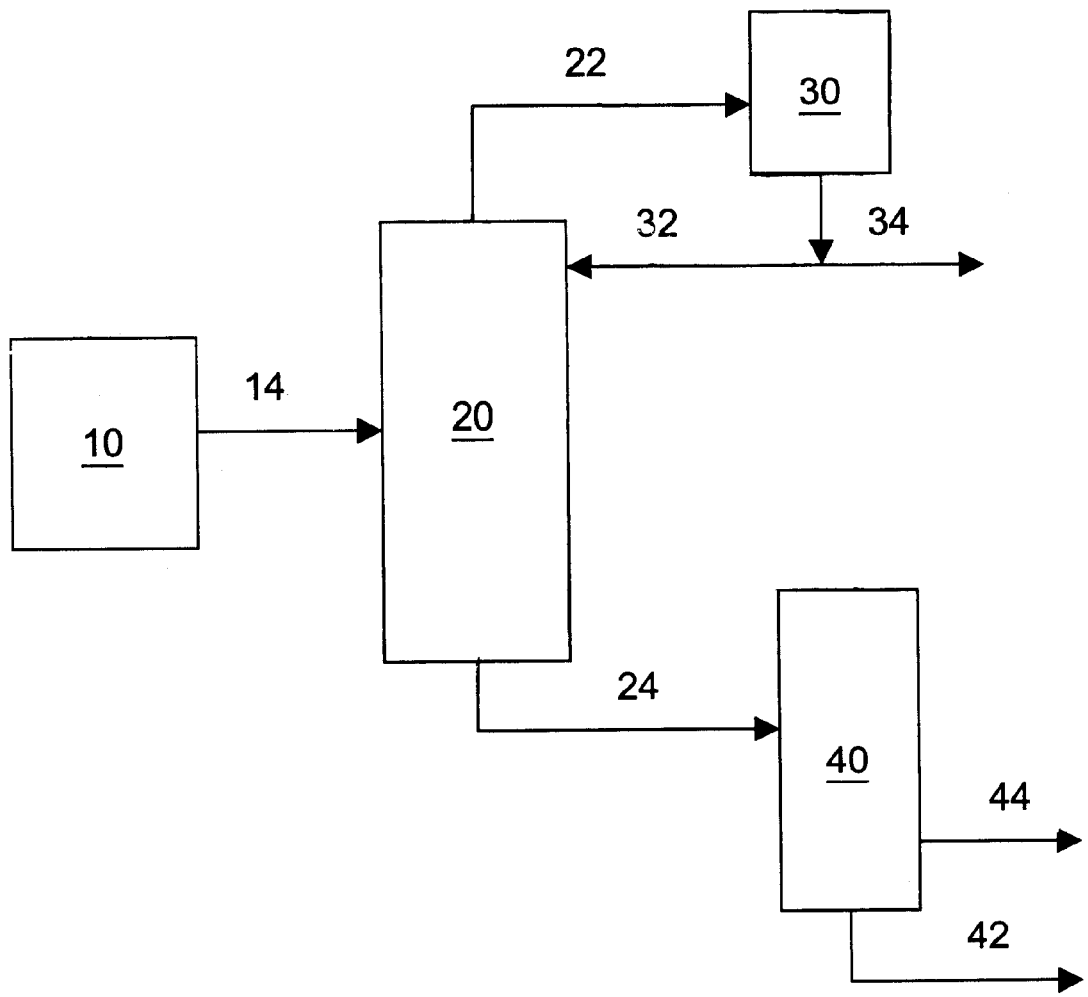

METHOD FOR PURIFYING FREE-BASE P-PHENYLENEDIAMINE-TYPE PHOTOGRAPHIC COLOR DEVELOPERS

BACKGROUND OF THE INVENTION

This invention pertains to a process for purifying p-phenylenediarnine-type color developers used in photographic color development and reproduction applications. More particularly, the present invention relates to a process for purifying p-phenylenediamine-type photographic color developers in their free-base that are substantially free of sulfate ions. This invention permits the preparation of useful solid and solution compositions of p-phenylenediamine color developers in the free-base form. In another embodiment of the present invention, the method provides an improved process for preparing p-phenylenediamine color developers in the acid salt form.

The basic processes for obtaining useful color images from exposed color photographic silver halide materials include several steps of photochemical processing such as color development, silver bleaching, silver halide fixing and water washing or dye image stabilizing using appropriate photochemical compositions.

The photofinishing industry is comprised of three primary segments: the manufacture of photographic chemicals to supply photochemical formulators, the formulation of these chemicals into useful compositions for photochemical processing, and the processing of sensitized photographic color elements. Formulated photographic processing (photofinishing) solutions provided to the processors are complex, multi-part, multi-component mixtures, the specific compositions of which vary significantly according to the intended use and the formulator.

The types of materials which are ultimately mixed by a photofinisher just prior to use and delivered to the photo processing bath include: solubilizing agents, e.g., organic co-solvents; bases for pH control; color developing agents or color developers; preservatives; antifoggants; sequestering agents; buffering agents; clarifying agents; stain-reducing agents; anti-bacterial or anti-fungal agents; surfactants; and other function-specific materials.

In conventional silver halide color photography, photofinishing solutions in the final processing bath includes a color developer, a preservative, and a solvent or combination of solvents. The color developer agent, in its free base form, serves to amplify the latent image on the silver halide crystals by reacting, in its oxidized form, with a dye-forming color coupler and subsequently, produce a color image of the exposed, sensitized photographic color element.

Suitable color developing agents that are known in the art include aromatic amino color developing agents such as p-phenylenediamines, and particularly the N,N-dialkyl-p-phenylenediamines in which the alkyl groups or the aromatic nucleus can be substituted or unsubstituted. The p-phenylenediamine color developers most commonly present in photofinishing compositions include: N,N-diethyl-2-methyl-p-phenylenediamine monohydrochloride (CD-2); N-ethyl-N-2-(methanesulfonylaminoethyl)-2-methyl-p-phenylenediamine sesquisulfate monohydrate (CD-3); and N-ethyl-N-(2-hydroxyethyl)-2methyl-p-phenylenediamine sulfate (CD-4), listed here in the commonly used acid salt is form.

Color developing compositions are commonly supplied in multiple parts or solutions because of the requirement to separate components which are reactive or unstable over extended periods of time. One part normally includes an acid salt of a p-phenylenediamine color developer, typically in the form of a stabilized aqueous solution. These solutions are acidic since the color developer is formulated in this part as the acid salt. Another part typically contains a base or combination of bases which, upon mixing of the parts, serves to neutralize the acid associated with the part containing the color developer and to establish the desired alkalinity of the mixed color developing composition. These solutions are typically mixed immediately before use. Upon combination of all parts and water, a homogeneous color developing composition can usually be obtained for the working strength solution in the processing machine.

There is a desire in the industry to reduce the number of parts used to prepare color developing compositions, and particularly to prepare replenishing solutions. A wide range of compositions are described in the art or commercially available as "ready to use" solutions, concentrates or dry formulations. Liquid concentrates have only to be diluted with water to provide a working strength solution. Dry formulations need only be dissolved in water.

The free-base forms of these color developers are presently industrially processed in solutions as non-isolated intermediates prepared from the acid salt form of the p-phenylenediamine. The free base form of the color developer is prepared by mixing an aqueous solution of the color developer salt with sodium hydroxide. For example, US Pat. Nos. 6,017,687 issued to Darmon et al. on Jan. 25, 2000 and 6,077,651 issued to Darmon et al. on Jun. 20, 2000 disclose a homogeneous, single-part, chloride ion-free color developing concentrate that is prepared using a critical sequence of steps. In the first step, an aqueous solution of the color developing agent is prepared typically from the sulfate salt and an alkali metal base to provide a stoichiometric proportion of alkali metal ions to render the color developer in a free base form. A disadvantage of obtaining the free base color developer in this manner is that an insoluble sulfate salt that precipitates from the solution. The solid precipitate must then be removed from the solution in an extra step. Additionally, due to the solubility of the sulfate salt there will always be some residual sulfate ions in solution, which these patents teach is detrimental to the composition stability of a photofinishing solution.

The use of such combined photofinishing solutions results in simplicity of operation with a reduction in the potential of mixing errors and poor photoprocessing results. The major incompatibility of the traditional parts of photofinishing solutions is that between the acidic aqueous part, containing the acid salt of the p-phenylenediamine color developer, and the alkaline part, containing the base or combination of bases. Since the active color developer in the final, mixed photofinishing composition is the free base form of the color developer, full consolidation of parts to produce a single-part formulation requires a source of the p-phenylenediamine color developer in free base form as the necessary ingredient. As used herein, the term "free-base" refers to phenylenediamine compounds devoid, or essentially devoid, of acid addition salts of phenylenediamines.

The preparation of N,N-disubstituted p-phenylenediamines has been known for many years; the earliest and most complete summary of the preparation of these compounds is found in the Journal of the American Chemical Society (Bent, Dessloch, Fassett, James, Ruby, Sterner, Vittum, and Weissberger, JACS 73, 3100–3125, 1951). For the synthesis of each of 61 N,N-disubstituted p-phenylenediamines, the last step was a reduction of either a nitroso, nitro, or an azo precursor. These nitroso, nitro, or azo precursors were subsequently reduced to the desired N,N-disubstituted p-phenylenediarnines (Free Bases) under the conditions of zinc and hydrochloric acid in water or by catalytic hydrogenation in ethyl alcohol. Generally, for the purposes of the present invention, the p-phenylenediamine free bases are prepared by the hydrogenation of a water-wet nitro or nitroso precursor in an alcohol solution in the presence of a heterogeneous hydrogenation catalyst under hydrogenation conditions of temperature and pressure. The heterogeneous catalyst is separated from the solution, providing p-phenylenediamine free base solutions with typical composition ranges of 25–40 weight percent p-phenylenediamine free base, 40–50 weight percent of the alcohol solvent, 15–25 weight percent water, and 2–6 percent (by difference) of total impurities. These intermediate free bases were purified by either crystallization or distillation, then converted to their more stable acid salt form.

Manufacturers of p-phenylenediamine color developers have avoided the use of traditional batch distillation process technology of the free base form due to oxidative and thermal degradation. Degradation by-products have been found to impart adverse effects on the photographic quality, rendering such distilled products unfit as a photographic color developer. A secondary factor in avoiding conventional distillation has been the low process yield.

Recovery of the p-phenylenediamine color developers by crystallization is also not without its problems. The resulting solution of the free base color developer is generally purified by contacting the solution with a decolorizing agent, such as activated carbon, which results in significant product yield losses to the decolorizing agent. Following decolorization, an appropriate mineral acid is added to the solution to convert the free base to its respective acid salt. The solution is cooled and the acid salt of the color developer is isolated by filtration. Although the filtrate typically contains a significant amount of the desired product, it is usually discarded due to the high concentration of impurities in the stream. In addition, the presence of water in the filtrate increases the solubility of the color developer acid salt and contributes to further yield losses to the filtrate. Typically, the isolated acid salt precipitate undergoes a re-crystallization step to achieve acceptable purity. Re-crystallization can be performed in an alcohol or ether solvent with a diminished yield loss, compared to the initial crystallization. The filtrate from this second crystallization is generally pure enough to permit the recycle of all or a significant portion of it. Accordingly, in current industry practice, there are significant yield losses which negatively impact the process economics and purity of the free base precursor to the acid salt.

There is a need for a process whereby direct purification and isolation of the color developer free base can be achieved with acceptable purity and which overcomes the yield losses and additional costs associated with current process technology.

SUMMARY OF THE INVENTION

The present invention provides a process for the purification of p-phenylenediamine color developers in their free-base form. The process includes the steps of subjecting a solution containing said free base color developer to short path distillation having a temperature less than about 250° C. and a pressure of less than about 10 mm of mercury and wherein said short path distillation includes at least one of falling film evaporator, thin film evaporator, wiped film evaporator, or short-path evaporator.

Yet another aspect of the present invention is an improved method for preparing an acid salt from the p-phenylenediamine free base color developer. The method includes the steps of: a) dissolving a purified p-phenylenediamine free base distillate in an organic solvent; b) contacting the dissolved free base distillate with an appropriate mineral acid; and c) crystallizing the color developer in the acid salt form.

It is an object of the present invention to provide a process for purifying p-phenylenediamine color developers, in their free-base form.

It is another object of the present invention to provide an improved method for preparing an acid salt of a p-phenylenediamine color developer.

These and other objects and advantages of the present invention will become more apparent to those skilled in the art in view of the following description and the accompanying drawing wherein like parts and objects have similar reference numerals. It is to be understood that the inventive concept is not to be considered limited to the constructions disclosed herein but instead by the scope of the appended claims.

BRIEF DESCRIPTION OF THE DRAWING

A schematic of a process for purifying a p-phenylenediamine color developer in accordance with the present invention.

DETAILED DESCRIPTION OF THE PREFERRED EMBODIMENTS

Photographic development is carried out by contacting an exposed photographic film with a color developing agent under suitable conditions of time and temperature and in suitable processing equipment. The aromatic primary amine color developing agents useful in the present invention include various known p-phenylenediamine derivatives. Especially preferred are the N,N-dialkyl-p-phenylenediamine derivatives wherein the alkyl groups or the alkenyl groups may independently include straight, branched or cyclic moieties. For example, their substitutes may include halogen atoms (such as F, Cl and Br), aryl groups (such as phenyl and p-chlorophenyl groups), alkoxy groups (such as methoxy, ethoxy and methoxyethoxy groups), aryloxy groups (such as phenoxy group), sulfonyl groups (such as methanesulfonyl and p-toluenesulfonyl groups), sulfonamido groups (such as methanesulfonamido and benzenesulfonamido groups), sulfamoyl groups (such as diethylsulfamoyl and unsubstituted sulfamoyl groups), carbamoyl groups (such as unsubstituted carbamoyl and diethylcarbamoyl groups), amido groups (such as acetamido and benzamido groups), ureido groups (such as methylureido and phenylureido groups), alkoxycarbonylamino groups (such as methoxycarbonylamino group), aryloxycarbonylamino groups (such as phenoxycarbonylamino group), alkoxycarbonyl groups (such as methoxycarbonyl group), aryloxycarbonyl groups (such as phenoxycarbonyl group), cyano group, hydroxy group, carboxy group, sulfo group, nitro group, amino groups (such as unsubstituted amino group and diethylamino group), alkylthio groups (such as methylthio group), arylthio groups (such as phenylthio group) and heterocyclic groups (such as morpholyl and pyridyl groups). Preferably, the p-phenylenediamine color developers which may be purified in accordance with the present invention in the free base form are: N,N-diethyl-2-methyl-p-phenylenediamine (CD-2 Free Base); N-ethyl-N-(2-methanesulfonylaminoethyl)-2-methyl-p- phenylenediamine (CD-3 Free Base); N-ethyl-N-(2-hydroxyethyl)-2-methyl-p-phenylenediamine (CD-4 Free Base) and mixtures thereof, (available from Eastman Chemical Company, Kingsport, TN).

Generally, the preparation of N,N-disubstituted p-pbenylenedi amines has been known for many years and the specific preparation of the crude free base solution is not considered to be part of the present invention. The earliest and most complete summary as to the preparation of these compounds is found in the Journal of the American Chemical Society (Bent, Dessloch, Fassett, James, Ruby, Sterner, Vittum, and Weissberger, JACS 73, 3100–3125, 1951). For the synthesis of each of 61 N,Ndisubstituted p-phenylenediamines, the last step was a reduction of either a nitroso, nitro, or an azo precursor. These nitroso, nitro, or azo precursors were subsequently reduced to the desired N,N-disubstituted p-phenylenediamines, i.e., the free base, using zinc and hydrochloric acid in water or by catalytic hydrogenation in ethyl alcohol.

For the purposes of the present invention, the p-phenylenediamine free bases are prepared by the hydrogenation of a water-wet nitro or nitroso precursor in an alcohol solution in the presence of a heterogeneous hydrogenation catalyst under hydrogenation conditions of temperature and pressure. The heterogeneous catalyst is separated from the solution, providing p-phenylenediamine free base solutions with typical composition ranges of 25–40 weight percent p-phenylenediamine free base, 40–50 weight percent of the alcohol solvent, 15–25 weight percent water, and 2–6 percent (by difference) of total impurities. In purifying the p-phenylenediamine free base according to the present invention, the crude p-phenylenediamine free base solution is subjected to short path distillation which includes at least one of falling film evaporator, thin film evaporator, wiped film evaporator, or short-path evaporator. Desirably, during short path distillation, the p-phenylenediamine free base material is subjected to temperatures less than about 250° C. and pressures less than about 10 mm of mercury for a time of from about 5 seconds to about 500 minutes. As used herein "short path distillation" refers to high vacuum, low contact time distillation technology that can include single or multiple configurations.

Referring to the figure, an embodiment of the present invention will be described in greater detail. The crude feed p-phenylenediamine free base is fed from tank 10 through line 14 to a thin film evaporator 20 to remove the relatively more volatile materials from the feed stream, such as the alcohol solvents, and water. These materials are removed via line 22 overhead and into condenser 30. The condenser may be a complete or partial condenser and have all or a portion of the condensate returned to the evaporator 20 via line 32. Optionally, the condensate may be removed from the purifying process via line 34. This material is then handled in a conventional manner, such as burning or recycling.

The thin film evaporator 20 desirably is operated at a temperature of from about 90° C. to about 240° C., and preferably from about 140° C. to about 220° C., and more preferably less than about 200° C. The operating pressure of the evaporator 20 is from about 0.001 mm of mercury to about 5 mm of mercury, and preferably from about 0.005 mm to about 1 mm of mercury.

The product from the thin film evaporator 20 is removed via line 24 and introduced into a short path evaporator 40. The short path evaporator 40 desirably is operated at a temperature of from about 90° C. to about 250° C., and preferably from about 140° C. to about 220° C., and more preferably less than about 200° C. The operating pressure of the evaporator 40 is from about 0.001 mm of mercury to about 5 mm of mercury, and preferably from about 0.005 mm to about 1 mm of mercury. Desirably, the concentration of the p-phenylenediamine free base in the product 42 is greater than about 90 weight %, and preferably greater than about 92 weight %, and more preferably, greater than about 95 weight %, and most preferably greater than about 97 weight %.

One skilled in the art will recognize that temperatures and pressures are directly related to each other in distillation separation process. Accordingly, one will recognize that as the operating pressure of the evaporators increases, the temperatures will increase accordingly. It is desirable in the refining of the p-phenylenediamine color developer that the temperature be less than about 200° C. and the pressure adjusted accordingly.

The residue 44 from the short path evaporator 40 is handled in a conventional manner. One skilled in the art will understand that although the short path distillation process described above utilized only one thin film evaporator and one short path evaporator, the process may further include plurality of such devices placed in series or parallel paths and further include falling film evaporators and wiped film evaporators.

It is critical to the distillation process that the p-phenylenediamine free base color developer be subjected to a temperature of not more than about 250° C. for a time not exceeding 30 minutes and preferably less than about 500 seconds. Desirably, the total time the p-phenylenediamine-type color developers in the short path distillation is from about 5 seconds to about 400 seconds and most preferably from about 20 seconds to about 300 seconds. Preferably, the p-phenylenediamine color developer is subjected to a temperature of less than about 220° C. for a time not exceeding 5 minutes. It is also critical that the operating pressure of the evaporators be less than about 10 mm of Hg, preferably less than about 5 mm of Hg and more preferably from about 0.001 to about 1 mm of Hg.

Advantageously, recovery of p-phenylenediamine free base color developer purified in accordance with the above process is from about 90 to 100% of the material in the crude feed. Moreover, the purified p-phenylenediamine free base color developer is substantially free of sulfate ions, having less than about 500 parts per million (ppm) of sulfate ions, preferably less than about 300 ppm of sulfate ions, more preferably less than about 50 ppm of sulfate ions and most preferably 0 (zero) sulfate ions. As used herein "substantially free of sulfate ions" means that the p-phenylenediamine free base color developer was not derived from a sulfate ion generating compound or that sulfate ions and/or a sulfate ion generating compound are purposefully added to the p-phenylenediamine free base color developer to form any part thereof into an acid salt of the p-phenylenediamine color developer.

An advantage of the present method of recovering color developers is that a single-part color developer concentrate that is substantially sulfate ion free can be prepared having: a) from about 10 to about 90 weight percent, preferably from about 10 to about 60 weight percent and more preferably from about 10 to about 40 weight percent of the p-phenylenediamine free base that is substantially sulfate ion free; b) about 1 to about 60 weight percent and preferably from about 1 to about 40 weight percent of a preservative; and c) about 10 to about 90 weight percent, preferably from about 10 to 70 weight percent and more preferably from about 10 to about 50 weight percent of a photographically inactive water-miscible or water-soluble hydroxy-containing organic solvent, wherein the aforementioned weight percentages are based on the total weights of (a), (b) and (c).

A single-part color developer concentrate as described above offers a number of advantages over the photochemical compositions currently available or known. Besides the advantages of being a concentrate, i.e., containing minimal water, considerable savings may be achieved in shipping and storage costs, and the concentrate is free of precipitates, slurries or multiple solvent phases. The concentrate does not require vigorous agitation prior to use and can be readily and immediately metered into a photofinishing solution formulation tank. A distinct advantage in preparing such a concentrate is that an acid salt of the p-phenylenediamine color developer is not formed into a solution which must thereafter be contacted with an alkali metal base to precipitate the sulfate ion in solution. Thus, the present invention results in reduced costs, by not having to add an alkali metal base material and filtering the resultant sulfate salt, and provides a superior p-phenylenediamine color developing concentrate that is substantially free of sulfate ions without having excess alkali metal ions in solution.

One or more antioxidants or preservatives can be included in the single part color developing concentrate described above in order to protect the color developing agents from-oxidation. The antioxidants can be either inorganic or organic. Many classes of useful antioxidants are known, including but not limited to, sulfites, such as sodium sulfite, potassium sulfite, sodium bisulfite, sodium metabisulfite and potassium metabisulfite, hydroxylamine and derivatives thereof, hydrazines, hydrazides, phenols, amino acids, ascorbic acid and derivatives thereof, hydroxamic acids, aminoketones, mono-and polysaccharides, mono- and polyamines, quaternary ammonium salts, nitroxy radicals, alcohols, and oximes. Especially useful antioxidants are hydroxylamine derivatives which include, but are not limited to N,N-bis(2,3-dihydroxypropyl)hydroxylamine, N,N-bis(2-methyl-2,3-dihydroxypropyl) hydroxylamine and N,N-bis(1-hydroxymethyl-2-hydroxy-3-phenylpropyl) hydroxylamine. The specific preservative or preservative combination used will depend upon the formulation and application.

Photographically inactive water-miscible or water-soluble hydroxy-containing organic solvents suitable for use in the single-part color developer concentrate includes solvents that are capable of dissolving one or more of the color developing agents in their free base form. For example, useful organic solvents include, but are not limited to, alkanols containing 2 to 8 carbon atoms such as ethyl alcohol, 1-propanol, 2-propanol, 1-butanol, 2-butanol, 2-methyl-1-propanol, 1-pentanol, 2-pentanol, 3-methyl-1-butanol, and 3-methyl-2-butanol; glycols containing 2 to 8 carbon atoms such as ethylene glycol, propylene glycol, 1,4-butanediol, 1,3-butanediol, 2-methyl-1,3-propanediol, 1,4-cyclohexanedimethanol, diethylene glycol, and triethylene glycol; polyethylene glycols such as PEG-200, PEG-300, PEG-400, and PEG-600; glycol ethers containing 3 to 8 carbon atoms such as 2-methoxyethanol, 2-ethoxyethanol, 2-propoxyethanol, 2-isopropoxyethanol, 2-butoxyethanol, 1-methoxy-2-propanol, 1-ethoxy-2-propanol, 3-meth6xy-1-butanol, dioxane, diethylene glycol monomethyl ether, diethylene glycol monoetbyl ether, diethylene glycol mono-n-propyl ether, diethylene glycol mono-1-propyl ether, diethylene glycol monobutyl ether, and triethylene glycol monomethyl ether; polyols such as glycerol; and polyol ethers containing 3 to 8 carbon atoms such as 3-methoxy-1,2-propanediol and 3-ethoxy-1,2-propanediol. Preferably, the solvent used is PEG-200, diethylene glycol, ethylene glycol, or propylene glycol. Such organic solvents can be used singularly or in combination.

The single-part color developer concentrate may contain other materials generally present in such color developing compositions. For example, the developer concentrate may include water, buffering agents, alkali metal halides, metal sequestering compositions, such as polycarboxylic or aminopolycarboxylic acids or polyphosphonates with or without lithium, magnesium or other small cations, auxiliary co-developing agents, such as phenidone type compounds particularly for black and white developing compositions, antifoggants, alkanolamines, development accelerators, optical brighteners, such as triazinylstilbene compounds, wetting agents, fragrances, stain reducing agents, surfactants, defoaming agents, and water-soluble or water-dispersible color couplers, as would be readily understood by one skilled in the art. The amounts of such additives are also well known in the art.

The color developer concentrates of this invention have utility to provide color development in an exposed photographic silver halide color paper comprising a support and one or more silver halide emulsion layers containing an image distribution of developable silver halide emulsion grains. In particular, the invention can be used to process color photographic papers of all types of emulsions. The layers of the color papers can have any useful binder material or vehicle as it known in the art, including various gelatins and other colloidal materials.

Color development of an image exposed photographic silver halide element is carried out by contacting the exposed color paper with a color developing composition prepared from the color developer concentrate of the present invention and under suitable time, temperature conditions, and in suitable processing equipment, to produce the desired developed image such as a color print. Additional processing steps can then be carried out using conventional procedures, including but not limited to, one or more development stop, bleaching, fixing, bleach/fixing, washing or rinsing, stabilizing and drying steps, in any particular desired order as would be known in the art.

The color papers processed can be a single layer or have a plurality of layered color elements. Multi-layer color papers typically contain dye image-forning units sensitive to each of the three primary regions of the visible spectrum. Each unit can be comprised of a single emulsion layer or multiple emulsion layers sensitive to a given region of the spectrum. The layers of the color paper can be arranged in any of the various orders known in the art. In an alternative format, the emulsions sensitive to each of the three primary regions of the spectrum can be disposed as a single segmented layer. The color papers can also contain other conventional layers such as filter layers, interlayers, subbing layers, overcoats and other layers readily apparent to one skilled in the art.

The processing time and temperature used for the various processing steps are generally those conventionally used in the art. For example, color development is generally carried out at a temperature of from about 20 to about 60° C. The overall color development time can be from about 75 to about 450 seconds. Shorter overall color development times are desired for processing color photographic papers in the industry especially in what are known as mini-labs. Such color development times may be as short as 5 seconds and as high as 60 seconds. Overall processing time, including color development, bleach-fixing and any rinsing steps of color papers using the single part color developing concentrate of this invention can be as long as 120 seconds, and as short as 30 seconds, and preferably from about 45 to about 90 seconds.

In yet another aspect of the present invention, an improved method for preparing p-phenylenediamine color developers in the conventional acid salt form is provided. The method includes contacting the purified p-phenylenediamine color developer obtained using the short path distillation process described above with an appropriate mineral acid; crystallizing the acid salt of the free base p-phenylenediamine color developer; and recovering the crystallized acid salt. Optionally, the crystallized acid salt can be dried. In a preferred embodiment, the filtrate is recycled back to the next batch for recovery of any solubilized p-phenylenediamine color developer.

Suitable mineral acids for forming the acid salt include, but are not limited to, sulfuric acid, hydrochloric acid, p-toluene sulfonic acid, phosphoric acid and mixtures thereof. The appropriate acid is added to convert the free base to the desired acid salt. The amount of acid required is from 1 to about 4.5 times the stoichiometric quantity and preferably, the amount of acid is about 1.02 to about 1.5 times the required amount. The acid may be added to the solvent before the introduction of the free base, or to the mixture of solvent and free base following mixing.

The present invention is illustrated in greater detail by the specific examples presented below. It is to be understood that these examples are illustrative embodiments and are not intended to be limiting of the invention, but rather are to be construed broadly within the scope and content of the appended claims. Unless otherwise indicated, all percentages are by weight.

EXAMPLE 1

A solution containing 32.5 weight percent N-ethyl-N-(2-rnethanesulfonylaminoethyl)-2-methyl-p-phenylenediamine, 22.5 weight percent water, 42.5 weight percent 2-propanol (solvent), and 2.5 weight percent impurities, was stripped of the organic solvent and water using an autoclave as a batch distillation unit.

The 2-propanol and water were removed to a final temperature of 110° C. and a final pressure of 10 mm Hg. The residue from the stripping unit was pumped continuously to a wiped film evaporator with a surface area of 0.15 $m^2$ at a flow rate of 200 g./hr. The wiped film evaporator is operated at a temperature of 200–217° C. and a pressure of 0.10 mbar. The distillate collected was 171.0 grams and had a product assay of 98.04%.

EXAMPLE 2

A solution of containing 32.5 weight percent N-ethyl-N-(2-methanesulfonylaminoethyl)-2-methyl-p-phenylenediamine, 22.5 weight percent water, 42.5 weight percent 2-propanol (solvent), and 2.5 weight percent impurities, was stripped of the organic solvent and water using an autoclave as a batch distillation unit. The 2-propanol and water were removed to a final temperature of 110° C. and a final pressure of 10 mm Hg. The residue from the stripping unit is fed continuously to a distillation train comprising: Stage 1) a thin-film evaporator (TFE) having a surface area of 0.1 $m^2$ and an external condenser operated at 150° C. and 4–7 mm pressure, functioning primarily as a degasser; Stage 2) a short-path wiped film evaporator (SPE) having a surface area of 0.15 $m^2$ with an internal condenser, graphite wiper blades, and splash guards; and Stage 3) a second short-path wiped film evaporator (SPE) equipped identically to the first SPE. The data from three trials following the description of this example and including the key operating parameters are shown in Table 1 below.

TABLE I

|  | Example No. | | |
| --- | --- | --- | --- |
|  | 2a | 2b | 2c |
| Configuration | 2-Stage SPE | 3-Stage SPE | 3-Stage SPE |
| Feed Rate (kg/hr) | 16.2 | 48.8 | 16.2 |
| Temperature (° C.) | 219 | 203 | 199 |
| Pressure (mbar) | 0.05 | 0.05 | 0.05 |
| Second Stage Yield (%) | 90.70 | 59.60 | 90.70 |
| Third State Yield (%) | — | 35.63 | 7.50 |
| Total Yield (%) | 90.70 | 95.23 | 98.20 |
| Assay | 98.8 | 98.5 | 98.2 |

EXAMPLE 3

An autoclave solution containing 34.8 weight percent N-ethyl-N-(2-hydroxyethyl)2-methyl-p-phenylenediamine, 15.4 weight percent water, 44.4 weight percent ethanol, and 5.4 weight percent impurities, is stripped of the organic solvent ethanol and water using a falling film evaporator (FFE) as a first stage. The FFE had a surface area of 0.3 $m^2$ and was run at 110° C. and 375 mm Hg pressure. The product residue from the first stage FFE unit, contained 86.6 weight percent N-ethyl-N-(2-hydroxyethyl)-2-methyl-p-phenylenediamine and 13.4 weight percent impurities. This material was continuously to fed to a thin-film evaporator (TFE) as a second stage. The TFE had a surface area of 0.1 $m^2$ with an external condenser operated at 110° C. and 14–18 mm Hg pressure, used primarily as a degasser. The stripped, degassed bottoms product from the second stage TFE was fed to third and fourth stage serial evaporators for further product distillation. The third stage was a short-path wiped film evaporator (SPE) having a surface area of 0.15 $m^2$ with an internal condenser, polytetrafluoroethylene (PTFE) wiper blades, and a splash guard. The fourth stage was a thin-film evaporator (TFE) having a surface area of 0.1 $m^2$ with PTFE wiper blades and an external condenser. The results are presented in Table II below.

EXAMPLE 4

In Example 4, the first two stages are the same as those described above for Example 3, however, both the third and fourth stages were short-path wiped film evaporators. Each had a surface area of 0.15 $m^2$ and was equipped with internal condenser, PTFE blades, and a splash guard. The results for Example 4 are shown in Table II below.

TABLE II

|  | Example No. | |
| --- | --- | --- |
|  | 3 | 4 |
| Configuration | 2-Stage SPE/TFE | 2-Stage SPE/SPE |
| Feed Rate (kg/hr) | 9.39 | 9.46 |
| Temperature (° C.) | 170 | 140 |
| Pressure (mbar) | 0.10 | 0.07 |
| Third Stage Yield (%) | 90.8 | 90.8 |
| Fourth Stage Yield (%) | 5.3 | 7.6 |
| Total Yield (%) | 96.1 | 98.4 |

In the following examples, solution compositions were prepared having a p-phenylenediamine color developer, purified in accordance with the present distillation process; in a water-soluble or water-miscible, hydroxy-containing organic solvent; and a preservative.

To define the free base solution product compositions, the solubility of the free base form of color developers N-ethyl-N-(2-methanesulfonylaminoethyl)-2-methyl-p-phenylenediamine and N-ethyl-N-(2-hydroxyethyl)-2-me determined in a number of potential solvents at ambient temperature, nominally 24° C. The free base form for the color developer N,N-diethyl-2-methyl-p-phenylenediamine was not evaluated because it is a liquid at ambient temperatures and fully miscible with all the water-soluble, water-miscible, hydroxy-containing solvent candidates.

A small quantity, about 3 weight % relative to the weight of the solvent, of N,N-diethylhydroxylamine (DEHA) was added as a preservative to each determination. Excess color developer free base identified above was added to each solvent and saturation was achieved by mixing for several hours at room temperature. The saturation concentration was determined in weight percent by the techniques of high pressure liquid chromatography (HPLC) and nuclear magnetic resonance (NMR), the results from each analytical technique being quite comparable.

Table III shows the saturation concentration of N-ethyl-N-(2-methanesulfonylaminoethyl)-2-methyl-p-phenylenediamine (Examples 5–14) and Nethyl-N-(2-hydroxyethyl)-2-methyl-p-phenylenediamine (Examples 15–20) in weight percent at ambient temperature in a variety of solvents. PEG-200 and PEG-300 refers to poly(ethylene glycol) having an average molecular weight of 200 and 300, respectively.

TABLE III

| Example No. | Solvent | Free Base Conc. (wt. %) |
|---|---|---|
| 5 | 2-Isopropoxyethanol | 8.6 |
| 6 | 2-Methyl-1,3-Propanediol | 3.3 |
| 7 | 3-Methoxy-1-butanol | 9.3 |
| 8 | PEG-200 | 16.9 |
| 9 | PEG-300 | 16.7 |
| 10 | Diethylene Glycol | 15.2 |
| 11 | N,N-Diethylhydroxylamine | 7.8 |
| 12 | Methanol | 23.6 |
| 13 | Ethanol | 5.4 |
| 14 | 2-Propanol | 1.8 |
| 15 | 2-Isopropoxyethanol | 32.6 |
| 16 | 2-Methyl-1,3-Propanediol | 33.2 |
| 17 | 3-Methoxy-1-butanol | 35.5 |
| 18 | PEG-200 | 31.0 |
| 19 | PEG-300 | 28.3 |
| 20 | Diethylene Glycol | 38.4 |

Examples 21 and 22 illustrate an improved process for preparing p-phenylenediamine color developer in their acid salt form. Low and consistent solution color of the color developer acid salt is important to photofinishing formulators. Product color is typically measured for color developers as absorptivity (mL/g-cm) in a 5 weight percent solution in 0.1 N aqueous sulfuric acid. The measurement wavelengths are 437 nanometers (nm) for N,N-diethyl-2-methyl-p-phenylenediamine monohydrochloride; 450 and 540 nm for N-ethyl-N-(2-methanesulfonylaminoethyl)-2-methyl-p-phenylenediamine sesquisulfate monohydrate; and 540 rn. for N-ethyl-N-(2-hydroxyethyl)-2-methyl-p-phenylenediamine sulfate. High purity of the color developer acid salt is also of importance to photofinishing formulators. The assay is typically measured by cerate titration of the p-phenylenediamine moiety. Finally, a clear final photofinishing solution, free of undissolved impurities in the form of particulates or oils, is another important criterion for the photofinishing formulators. To quantify performance relative to clarity of a photofinishing solution for N-ethyl-N-(2methanesulfonylaminoethyl)-2-methyl-p-phenylenediamine sesquisulfate monohydrate, turbidity in nephalometric turbidity units (NTU) is measured in a fully mixed Kodak Ektachrome R-3 Color Developer Replenisher matrix, one known for its sensitivity and discrimination to N-ethyl-N-(2methanesulfonylaminoethyl)-2-methyl-p-phenylenediamine sesquisulfalte monohydrate quality and purity.

EXAMPLE 21

A three-neck, 2 liter round bottom flask contained 171.0 g. of N-ethyl-N(2methanesulfonylaminoethyl)-2-methyl-p-phenylenediamine (assay 98.0%, 0.618 moles), and was equipped with an overhead agitator, an addition funnel, and a reflux condenser. The flask was carefully purged with nitrogen to remove any residual oxygen. The flask was charged with 1 kilogram of 2propanol and 100 g of water. The solution was agitated at room temperature for about ten minutes. The addition funnel was charged with 96% sulfuric acid (143.0 g., 1.400 moles). The sulfuric acid was added to the free base solution over a period of 30 minutes, allowing the temperature to rise to about 45–50° C. The solution was then heated to 75° C., and held at this temperature for 30 minutes. The solution was thereafter cooled to 10° C. over a two hour period. The acid salt product, N-ethyl-N-(2methanesulfonylaminoethyl)-2-methyl-p-phenylenediamine sesquisulfate monohydrate, was formed as a white precipitate. The solids were isolated by filtration, then washed with 2propanol having a temperature of about 0–20° C. The solids were dried at 60° C. and under 10 mm psia for 16 hours. The dried N-ethyl-N (2methanesulfonylaminoethyl)-2-methyl-p-phenylenediamine sesquisulfate monohydrate product, a white crystalline material, weighed 265.0 g. (0.607 moles, 98.2% yield from free base). The data for the isolation of N-ethyl-N-(2methanesulfonylaminoethyl)-2-methyl-p-phenylcnediaminc sesquisulfate monohydrate in three separate experiments from distilled, purified, N-ethyl-N-(2methanesulfonylaminoethyl)-2-methyl-p-phenylenediamine by the process described above are shown in Table IV below.

TABLE IV

| | Absorptivity (mL/g-cm) | |
|---|---|---|
| Measured Property | Distilled Process | Conventional Crystallization |
| Absorptivity (450 nm) | 0.21–0.33 | 0.39 |
| Absorptivity (540 nm) | 0.12–0.20 | 0.24 |
| Assay (%) | 100.5–101.2 | 100.3 |
| Turbidity (NTU) | 1–2 | 10.6 |
| Free Base Recovery (%) | 94–98 | 90 |

EXAMPLE 22

A three-neck, 5 liter round bottom flask contained 328.0 g. of N-ethyl-N2hydroxyethyl)-2-methyl-p-phenylenediamine (assay 98.0%, 1.655 moles), and was equipped with an overhead agitator, an addition funnel, and a reflux condenser. The flask was carefully purged with nitrogen to remove any residual oxygen. The flask was charged with 2,150 g of anhydrous ethyl alcohol and 32 g of water. The solution was agitated at room temperature for ten minutes. The addition funnel was charged with 96% sulfuric acid (185.4 g., 1.815 moles). The sulfuric acid was added to the free base solution over a period of 30 minutes, allowing the temperature to rise to about 45–50° C. The solution was then heated to 75° C., and held at this temperature for 30 minutes. The solution was thereafter cooled to 10° C. over a two hour period. The acid salt product, N-ethyl-N (2hydroxyethyl)-2-methyl-p-phenylenediamine sulfate, was formed as a white precipitate. The solids were isolated by filtration, then washed with ethyl alcohol having a temperature of about 0–20° C. The solids were dried at 60° C. and under 10 mm psia for 16 hours. The dried N-ethyl-N-(2hydroxyethyl)-2-methyl-p-phenylenediamine sulfate, a white crystalline material, weighed 455.0 g. (1.556 moles, 94.0% yield from free base). The data for the isolation of CD-4 acid salt in three separate experiments from distilled, purified, N-ethyl-N-(2hydroxyethyl)-2-methyl-p-phenylenediamine by the process described above are shown in Table V below.

TABLE V

| Measured Property | Absorptivity (mL/g-cm) | |
| --- | --- | --- |
|  | Distilled Process | Conventional Crystallization |
| Absorptivity (540 nm) | 0.11–0.20 | 0.32 |
| Assay (%) | 100.0–100.3 | 99.8 |
| Free Base Recovery (%) | 92–95 | 84 |

From the above one will readily recognize the improved process allows the conversion of the purified, distilled free base into the acid salt form to be performed directly without any decolorizing step and the associated yield losses, i.e., having a yield where greater than about 92 % of the p-phenylenediamine color developer is converted to the respective acid salt. Moreover, because of the high purity of the distilled free base and the associated low levels of impurities, a significant portion of the filtrate may be returned to a crystallizer and recycled to the next batch. Thus, it is not necessary to perform two crystallization steps to improve purity and achieve fitness-for-use is required.

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

We claim:

1. A process for purifying p-phenylenediamine-type color developers in their free-base form comprising subjecting a solution containing said free base color developer to short path distillation having a temperature less than about 250° C., a contact time less than about 30 minutes and a pressure of less than about 10 mm of Hg and wherein said short path distillation includes at least one of a falling film evaporator, a thin film evaporator, a wiped film evaporator, or a short-path evaporator.

2. The process of claim 1 wherein said free base color developer is subjected to a temperature of from about 90° C. to about 240° C., and a pressure from about 0.001 mm of mercury to about 5 mm of mercury for a time of from about 5 seconds to about 400 seconds.

3. The process of claim 1 wherein said free base color developer is subjected to a temperature less than about 200° C., and a pressure from about 0.005 mm to about 1 mm of mercury for a time of from about 20 seconds to about 300 seconds.

4. The process of claim 1 wherein said p-phenylenediamine free base color developer is selected from the group consisting of N,N-dialkyl-p-phenylenediamine derivatives wherein said alkyl moiety and said alkenyl moiety may independently be selected from the group consisting of F, Cl, Br, phenyl, p-chlorophenyl, methoxy, ethoxy, methoxyethoxy, phenoxy, sulfonyl, methanesulfonyl, p-toluenesulfonyl, methanesulfonamido, benzenesulfonamido, diethylsulfamoyl, unsubstituted sulfamoyl moieties, unsubstituted carbamoyl moieties, diethylcarbamoyl moieties, acetamido moieties, benzamido moieties, methylureido, phenylureido moieties, methoxycarbonylamino moieties, aryloxycarbonylamino moieties, methoxycarbonyl moiety, phenoxycarbonyl moieties, cyano moieties, hydroxy moieties, carboxy moieties, sulfo moieties, nitro moieties, amino moieties, diethylamino moieties, methylthio moieties, phenylthio moieties, morpholyl moieties, and pyridyl moieties.

5. The process of claim 1 wherein said p-phenylenediamine free base color developer is selected from the group consisting of N,N-diethyl-2-methyl-p-phenylenediamine, N-ethyl-N-(2-methanesulfonylaminoethyl)-2-methyl-p-phenylenediamine, N-ethyl-N-(2hydroxyethyl)-2-methyl-p-phenylenediamine and mixtures thereof.

6. The process of claim 1 wherein said purified p-phenylenediamine-type color developer has a purity greater than about 90 weight %.

7. The process of claim 1 wherein said purified p-phenylenediamine-type color developer has a purity greater than about 92 weight %.

8. The process of claim 1 wherein said purified p-phenylenediamine-type color developer has a purity greater than about 95 weight %.

9. The process of claim 1 wherein said purified p-phenylenediamine-type color developer has a purity greater than about 97 weight %.

10. A process for purifying p-phenylenediamine-type color developers in their free-base form comprising subjecting a solution containing said free base color developer to short path distillation having a temperature of from about 140° C. to about 220° C., and a pressure from about 0.001 mm of mercury to about 5 mm of mercury for a time of from about 5 seconds to about 400 seconds and wherein said short path distillation includes at least one of a falling film evaporator, a thin film evaporator, a wiped film evaporator, or a short-path evaporator.

11. The process of claim 10 wherein said free base color developer is subjected to a temperature less than about 220° C., and a pressure from about 0.005 mm to about 1 mm of mercury for a time of from about 20 seconds to about 300 seconds.

12. The process of claim 10 wherein said p-phenylenediamine free base color developer is selected from the group consisting of N,N-diethyl-2-methyl-p-phenylenediamine, N-ethyl-N-(2methanesulfonylaminoethyl)-2-methyl-p-phenylenediamine, N-ethy-N-(2hydroxyethyl)-2-methyl-p-phenylenediamine and mixtures thereof.

13. The process of claim 10 wherein said purified p-phenylenediamine-type color developer has a purity greater than about 95 weight %.

* * * * *

UNITED STATES PATENT AND TRADEMARK OFFICE
CERTIFICATE OF CORRECTION

PATENT NO. : 6,492,099 B1
DATED : December 10, 2002
INVENTOR(S) : Lucian Boldea and Phillip Montgomery Hudnall Page 1 of 2

It is certified that error appears in the above-identified patent and that said Letters Patent is hereby corrected as shown below:

Column 1,
Line 62, delete "N-ethyl-N-(2-hydroxyethyl)-2methyl-p- phenylenediamine sulfate" and insert -- N-ethyl-N-(2-hydroxyethyl)-2-methyl-p-phenylenediamine sulfate -- therefor.

Column 7,
Line 62, delete "3-meth6xy-1-butanol" and insert -- 3-methoxy-1-butanol -- therefor.
Line 64, delete "monoetbyl ether" and insert -- monoethyl ether -- therefor.

Column 8,
Line 47, delete "image-forning" and insert -- image-forming -- therefor.

Column 9,
Lines 39 and 40, delete "N-ethyl-N-(2-rnethanesulfonylaminoethyl)-2-methyl-p-phenylenediamine" and insert -- N-ethyl-N-(2-methanesulfonylamino ethyl)-2-methyl-p-phenylenediamine -- therefor.

Column 11,
Line 7 delete "N-ethyl-N-(2-hydroxyethyl)-2-me" and insert -- N-ethyl-N-(2-hydroxyethyl)-2-methyl-p-phenylenediamine was -- therefor.
Line 26, delete "Nethyl-N-(2-hydroxyethyl)-2-methyl-p-phenylenediamine" and insert -- N-ethyl-N-(2-hydroxyethyl)-2-methyl-p-phenylenediamine -- therefor.
Line 61, delete "540 rn" and insert -- 540 nm -- therefor.

Column 12,
Line 16, delete "N-ethyl-N(2methanesulfonylaminoethyl)-2-methyl-p-phenylenediamine" and insert -- N-ethyl-N-(2-methanesulfonylaminoethyl)-2-methyl-p-phenylenediamine -- therefor.
Line 20, delete "2propanol" and insert -- 2-propanol -- therefor.
Line 29, delete N-ethyl-N-(2methanesulfonylaminoethyl)-2-methyl-p-phenylenediamine sesquisulfate monohydrate" and insert -- N-ethyl-N-(2-methanesulfonylaminoethyl)-2-methyl-p-phenylenediamine sesquisulfate monohydrate -- therefor.
Line 33, delete "2propanol" and insert -- 2-propanol -- therefor.
Line 35, delete "N-ethyl-N(2methanesulfonylaminoethyl)-2-methyl-p-phenylenediamine sesquisulfate monohydrate" and insert -- N-ethyl-N-(2-methanesulfonylaminoethyl)-2-methyl-p-phenylenediamine sesquisulfate monohydrate -- therefor.
Lines 39 and 40, delete "N-ethyl-N-(2methanesulfonylaminoethyl)-2-methyl-p-phenylcnediaminc sesquisulfate monohydrate" and insert -- N-ethyl-N-(2-methanesulfonylaminoethyl)-2-methyl-p-phenylenediamine sesquisulfate monohydrate -- therefor.

UNITED STATES PATENT AND TRADEMARK OFFICE
CERTIFICATE OF CORRECTION

PATENT NO.   : 6,492,099 B1
DATED        : December 10, 2002
INVENTOR(S)  : Lucian Boldea and Phillip Montgomery Hudnall It is certified that error appears in the above-identified patent and that said Letters Patent is hereby corrected as shown below:

Column 12 (cont'd),
Line 42, delete "N-ethyl-N-(2methanesulfonylaminoethyl)-2-methyl-p-phenylenediamine" and insert -- N-ethyl-N-(2-methanesulfonylaminoethyl)-2-methyl-p-phenylenediamine -- therefor.
Line 60, delete "N-ethyl-N2hydroxyethyl)-2-methyl-p-phenylenediamine" and insert -- N-ethyl-N-(2-hydroxyethyl)-2-methyl-p-phenylenediamine -- therefor.

Column 13,
Line 7, delete "N-ethyl-N-(2hydroxyethyl)-2-methyl-p-phenylenediamine sulfate" and insert -- N-ethyl-N-(2-hydroxyethyl)-2-methyl-p-phenyplenediamine sulfate -- therefor.
Lines 11 and 12, delete "N-ethyl-N-(2hydroxyethyl)-2-methyl-p-phenylenediamine sulfate" and insert -- N-ethyl-N-(2-hydroxyethyl)-2-methyl-p-phenylenediamine sulfate -- therefor.

Column 13, line 16 and Column 14, line 28,
Delete "N-ethyl-N-(2hydroxyethyl)-2-methyl-p-phenylenediamine" and insert -- N-ethyl-N-(2-hydroxyethyl)-2-methyl-p-phenylenediamine -- therefor.

Column 14,
Line 60, delete "N-ethyl-N-(2methanesulfonylaminoethyl)-" and insert -- N-ethyl-N-(2-methanesulfonylaminoethyl)- -- therefor.
Line 61, delete "N-ethy-N-(2hydroxyethyl)-" and insert -- N-ethyl-N-(2-hydroxyethyl)- -- therefor.

Signed and Sealed this

Twenty-second Day of April, 2003

JAMES E. ROGAN
*Director of the United States Patent and Trademark Office*